United States Patent

Hedberg et al.

Patent Number: 5,464,429
Date of Patent: * Nov. 7, 1995

[54] APPARATUS FOR PRODUCING HEART DEFIBRILLATION SEQUENCES FROM STIMULATION PULSES AND DEFIBRILLATION SHOCKS

[75] Inventors: Sven-Erik Hedberg, Kungsaengen; Martin Obel, Danderyd; Kurt Hoegnelid, Villavägen, all of Sweden

[73] Assignee: Pacesetter AB, Solna, Sweden

[ * ] Notice: The portion of the term of this patent subsequent to Jul. 11, 2012, has been disclaimed.

[21] Appl. No.: 114,357

[22] Filed: Sep. 1, 1993

[30] Foreign Application Priority Data

Sep. 16, 1992 [SE] Sweden ................................. 9202662

[51] Int. Cl.6 .................................................. A61N 1/362
[52] U.S. Cl. ............................................................ 607/4
[58] Field of Search ................................................ 607/4, 5

[56] References Cited

U.S. PATENT DOCUMENTS

| | | |
|---|---|---|
| 4,549,548 | 10/1985 | Wittkampf et al. . |
| 5,007,422 | 4/1991 | Pless et al. . |
| 5,063,928 | 11/1991 | Grevis et al. . |
| 5,105,810 | 4/1992 | Collins et al. . |
| 5,111,816 | 5/1992 | Pless et al. . |
| 5,133,353 | 7/1992 | Hauser ................................. 607/4 |
| 5,314,448 | 5/1994 | Kroll et al. ........................... 607/5 |
| 5,324,309 | 6/1994 | Kallok ................................... 607/5 |

Primary Examiner—William E. Kamm
Assistant Examiner—Marianne Parker
Attorney, Agent, or Firm—Hill, Steadman & Simpson

[57] ABSTRACT

An apparatus for producing heart defibrillation sequences formed of stimulation pulses and defibrillation shocks contains a unit for delivering pulses through an intracardiac or epicardiac electrode, normally for cardiac pacing, and defibrillator circuitry for delivering defibrillation shocks through defibrillation electrodes. The unit for delivering pacing pulses has an output stage which is capable of generating a stimulation pulse, delivered to the heart via the pacing electrode, having a higher energy content than a pacing pulse, but considerably less energy than a conventional defibrillation shock. A control unit is connected to the unit for delivering stimulation pulses and to the defibrillator circuitry for forming a defibrillation sequence consisting of stimulation pulses and defibrillation shocks. The control unit determines the timing for delivering the stimulation pulses and the defibrillation shocks.

20 Claims, 2 Drawing Sheets

APPARATUS FOR PRODUCING HEART DEFIBRILLATION SEQUENCES FROM STIMULATION PULSES AND DEFIBRILLATION SHOCKS

BACKGROUND OF THE INVENTION

1. Field of the Invention

This invention relates to implantable devices for pacing and, when necessary, defibrillating a heart.

2. Description of the Prior Art

Heart defibrillation is currently performed by the discharge of a powerful voltage pulse between two electrodes. The electrodes are placed so the discharge takes place over the heart or a large part thereof. The energy in a pulse amounts typically to several to a few dozen joules.

The large energy required in the defibrillation pulse has shortcomings. For implantable devices with both defibrillation and pacemaker functions, i.e. devices designed to normally operate as pacemakers, the high energy consumed in defibrillation shortens the life of the apparatus considerably. The powerful energy discharge also has certain adverse effects on the organism.

SUMMARY OF THE INVENTION

An object of the present invention is to reduce shortcomings in known heart defibrillation techniques and to provide an apparatus which makes defibrillation possible with less energy.

In the apparatus according to the invention, the above objects achieved by delivering stimulation pulses through an intracardiac or epicardiac electrode normally used for pacing. These stimulation pulses achieve part of the heart's defibrillation, i.e. primarily in the area around the stimulation electrode employed. Other parts of the heart are defibrillated with defibrillation shocks in the customary manner. In this way, effective defibrillation can be achieved with considerably less defibrillation energy than has hitherto been possible. The stimulation pulses used can be high-energy stimulation pulses with an amplitude and/or pulse duration which greatly exceed the amplitude and/or pulse duration of ordinary pacemaker pulses, however, the high-energy stimulation pulses contain considerably less energy than an ordinary defibrillation pulse, thereby reducing the total energy consumption.

According to one embodiment of the invention, the control unit contains a memory, in which information is stored about the times for delivering stimulation pulses and defibrillation shocks respectively, and about the duration and amplitudes of the stimulation pulses and defibrillation shocks in each defibrillation sequence. A microprocessor controls the control unit for delivering stimulation pulses and the defibrillator circuitry on the basis of the stored information. This information is suitably stored in the form of data, programmed by a physician, which are adapted to the condition of each patient. Switching between stimulation pulses and defibrillation shocks is also controlled on the basis of the stored data. The start of a defibrillation sequence is performed in the same way as in the emission of a shock by a defibrillator according to the prior art.

According to another embodiment of the apparatus of the invention, an electrode switching unit is arranged to connect, in an optional manner, one of a plurality of possible electrodes for use as the return electrode for stimulation pulses. Thus, the case of the apparatus or a defibrillation electrode can serve as the return electrode. In this way, current from the stimulation pulses can be returned by different pathways through the heart at different times by shifting the return electrode, or the indifferent electrode, the stimulation pulses thereby covering larger areas.

According to yet another embodiment of the apparatus of the invention, the memory contains information about which electrode shall be connected as the return electrode, and the microprocessor of the control unit controls the electrode switching unit on the basis of this stored information. The return electrode can be shifted between each stimulation pulse or between groups of such stimulation pulses in the defibrillation sequence.

According to another embodiment of the apparatus of the invention, the control unit controls the unit for delivering stimulation pulses and the defibrillator circuitry so a series of stimulation pulses are emitted prior to each defibrillation shock. This produces a refractory area around the stimulation electrode for stopping fibrillation activity before the actual defibrillation shock is delivered. However, stimulation pulses in each defibrillation sequence can also be emitted between defibrillation shocks or after the same. The duration of a defibrillation sequence is on the order of one second.

In another embodiment of the invention, the stimulation electrode is an endocardiac or epicardiac electrode, and the defibrillation electrodes consist of patches, intracardiac electrodes or combinations thereof. The existing pacemaker electrode is used as the stimulation electrode.

In another embodiment of the invention, the magnitude of the energy in a high-energy stimulation pulse is on the order of one millijoule. A conventional stimulation pulse, delivered by a pacemaker, has a typical voltage of 10 V, a current of 10 mA and a duration of 1 ms, i.e. the pulse energy typically amounts to 100 µJ. Since the energy in a typical defibrillation shock is of the order of several dozen J, the high-energy stimulation pulses at the invention contain far more energy than conventional stimulation pulses from a pacemaker, but their energy is simultaneously well below the energy in a defibrillation shock.

DESCRIPTION OF THE PREFERRED EMBODIMENTS

Figure 1:
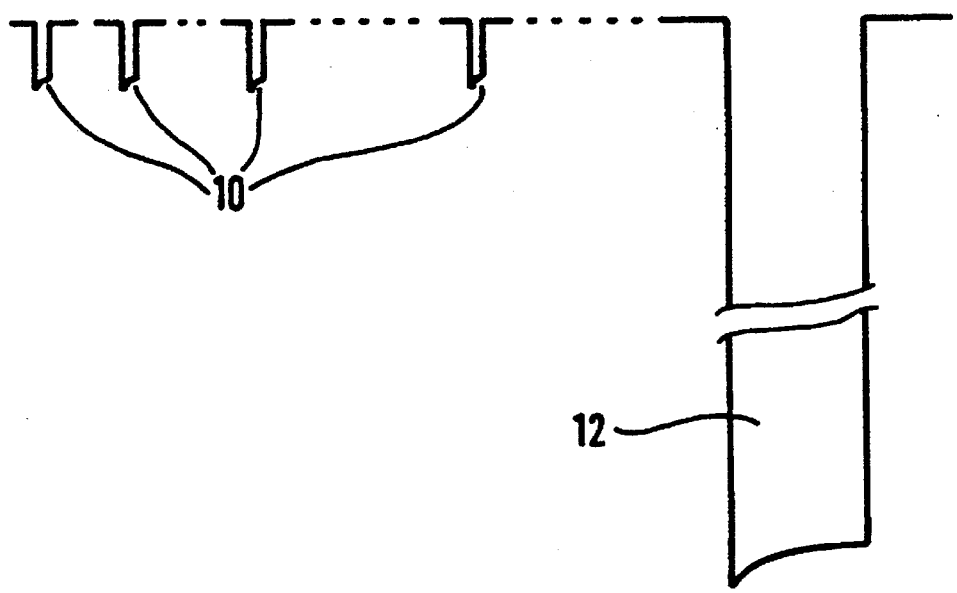
FIGS. 1 and 2 show parts of defibrillation sequences with different combinations of stimulation pulses and defibrillation shocks, in accordance with the principles of the present invention.
Figure 2:
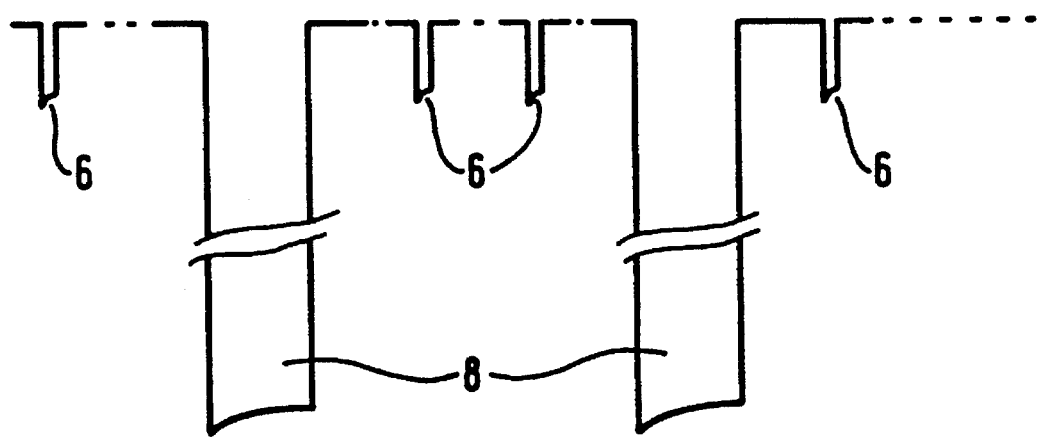

In FIG. 1 a part of an inventive defibrillation sequence with a plurality of high-energy type stimulation pulses 10 preceding a defibrillation shock 12 is shown. FIG. 2 shows a part of an inventive defibrillation sequence with high-energy stimulation pulses 6 before, between and after defibrillation shocks 8. In certain instances, having a number of high-energy stimulation pulses 10 precede the defibrillation shock 12, as illustrated in FIG. 1, may be appropriate, so the high-energy stimulation pulses 10 assure creation of a refractory area around the stimulation electrode before the defibrillation shock 12 is delivered, but, according to the invention, stimulation pulses and defibrillation shocks can be combined in defibrillation sequences in an optional fashion.

The high-energy stimulation pulses have an amplitude and/or pulse duration which greatly exceed the values for conventional stimulation pulses. However, the amplitude and pulse duration of the high-energy stimulation pulses are far less than the corresponding values for defibrillation pulses or shocks.

As illustrated in FIGS. 1 and 2, the time elapsing between the stimulation pulses 6 and 10 can also vary. The time between two consecutive stimulation pulses typically constitutes a fraction of the refractory period for a cardiac tissue cell, i.e. 20–200 ms.

Chronological relationships, not solely the pulse magnitude, are important to the impact on a patient's treatment and should be adapted to the patient's condition.

The pulse morphology shown in FIGS. 1 and 2 is only one example, and pulses with numerous other morphologies could be utilized.

Figure 3:
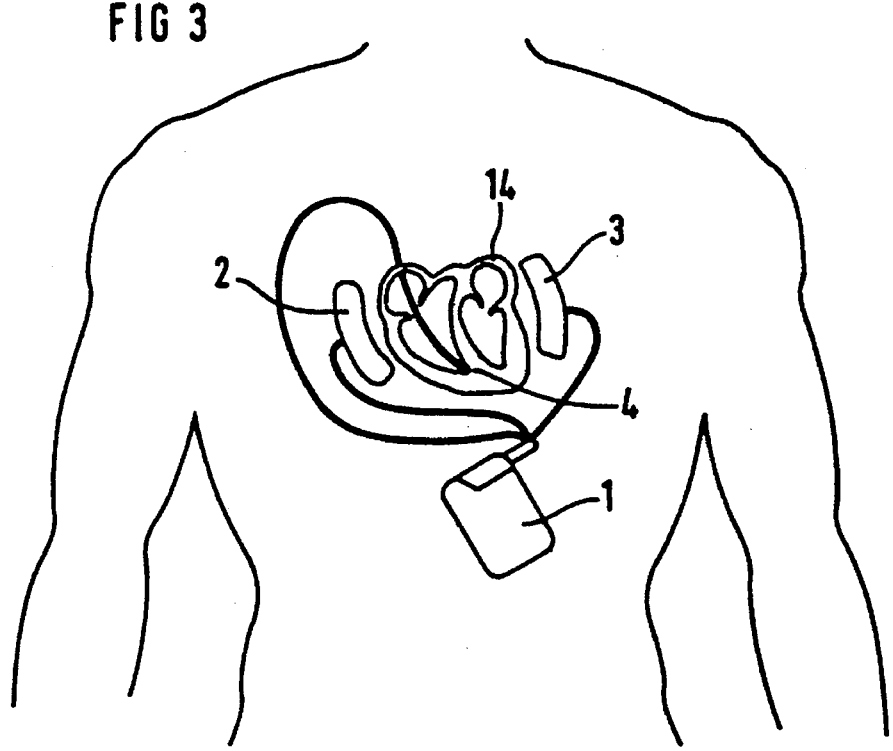
FIG. 3 shows an example of a defibrillation system constructed in accordance with the principles of the present invention, implanted in a patient.

FIG. 3 shows an example of a defibrillation system with pacing capability and equipped with a defibrillation apparatus according to the invention, implanted in a patient.

The defibrillator itself is shown at 1. Defibrillation pulses are delivered between two patch electrodes 2 and 3 arranged on either side of the heart 14. Stimulation pulses for conventional pacemaker operation, like the high-energy stimulation pulses emitted by the apparatus according to the invention, are delivered through the tip of the stimulation electrode 4 to the apex of the right ventricle. The electrode 4 employed for conventional pacemaker stimulation is also used to deliver stimulation pulses generated by the apparatus according to the invention.

Figure 4:
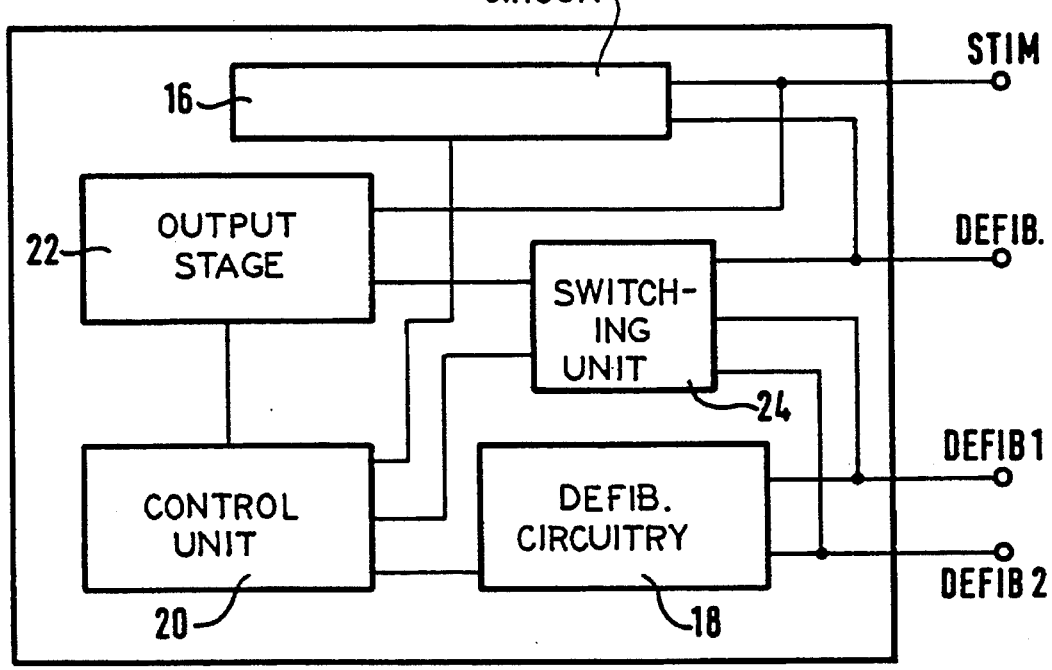
FIG. 4 is a block diagram of an example of the apparatus realized according to the invention.

A block diagram in FIG. 4 shows a version of the invention with a defibrillator with built-in pacing capability.

The defibrillator contains a pacemaker circuit 16 which delivers conventional pacemaker pulses through the stimulation electrode 4. Further, there is defibrillator circuitry 18 which delivers defibrillation pulses or shocks through two defibrillation electrodes 2 and 3 in the known manner. Both these circuits 16 and 18 are controlled by a common control unit 20.

The defibrillator also includes an output stage 22 for delivering high-energy pulses to the stimulation electrode 4. The output stage 22 is devised in a way similar to defibrillator circuitry 18, however, it operates with lower voltages, and the energy-storing capacitors for stimulation pulses have a lower capacitance than the capacitors in the defibrillator stage 18.

The control unit 20 contains a memory in which information is stored as to the times for delivering stimulation pulses and defibrillation shocks respectively, and the durations and amplitudes of the pulses and shocks. The combination of pulses and shocks in each defibrillation sequence can also be entered in the memory by external programming. The control unit 20 further contains a microprocessor which retrieves the requisite information from the memory in order to control the emission of stimulation pulses from the output stage 22 and defibrillation shocks from the circuitry 18.

The start of a defibrillation sequence can be made in the same way as when a defibrillation shock is to delivered by a conventional defibrillator.

Different electrodes, such as the patch electrodes 2 and/or 3 or the defibrillator case 1 itself, can serve as the return lead for stimulation pulses. The apparatus therefore contains an electrode switching unit 24 for selecting the return electrode. The electrode switching unit 24 is also controlled by the control unit 20, and information on the electrode to be connected as the return electrode can be stored in the memory of the control unit 20. The electrode switching unit 24 can be controlled so the different return electrodes are connected between each high-energy stimulation pulse, or between groups of such stimulation pulses in the defibrillation sequence. Such a procedure is highly advantageous. When shifted between different return electrodes, the pulse current passes through heart tissue by different pathways at different times, so the stimulation pulses reach a larger area.

The electrode selected by the control unit 20 will thus be connected by the electrode switching unit 24 to the output stage 22 for returning current from the patient. Switches in the electrode switching unit 24 suitably consist of transistors. These switch components must be dimensioned to withstand the high voltages a defibrillation shock can generate.

After the defibrillation sequence, the output stage 22 is disconnected from the STIM-connection of the pacemaker circuitry 16, and the return is switched off by the switches in the electrode switching unit 24 assume a high-impedance state.

The STIM connection in FIG. 4 is intended for connection to the stimulation electrode 4 in FIG. 3, the DEFIB connection to the patch 2 and the DEFIB2 connection to the patch 3.

The intracardiac stimulation electrode for the apparatus according to the invention can be an endocardiac or epicardiac electrode, and the embodiment exemplified above has defibrillation electrodes in the form of patches. However, intracardiac defibrillation electrodes, or combinations of such electrodes and patches, can be utilized.

Although modifications and changes may be suggested by those skilled in the art, it is the intention of the inventors to embody within the patent warranted hereon all variations as reasonably and properly come within the scope of their contribution to the art.

We claim as our invention:

1. An apparatus for defibrillation of a heart comprising:

a pacing electrode and a plurality of defibrillation electrodes;

means for delivering pacing pulses through said pacing electrode to a heart for pacing said heart;

means for delivering defibrillation shocks through said plurality of defibrillation electrodes to said heart;

output means, connected to said pacing electrode, for delivering stimulation pulses to said heart having an energy content slightly higher than said pacing pulses and significantly lower than said defibrillator shocks; and control means, connected to said means for delivering defibrillation shocks and to said output means, for producing a defibrillation sequence consisting of stimulation pulses and defibrillation shocks, respectively delivered to said heart via said pacing electrode and said defibrillation electrodes, at selected time intervals within said sequence.

2. An apparatus as claimed in claim 1 wherein said control means includes memory means for storing data for a plurality of respective time intervals available for delivering stimulation pulses and defibrillation shocks and for storing a plurality of available amplitudes of said stimulation pulses and defibrillation shocks and for storing a plurality of different available combinations of numbers and ordering of stimulation pulses and defibrillation shocks and microprocessor means for controlling delivery of said stimulation pulses and said defibrillation shocks by selecting from said memory means at least one of said available time intervals, available amplitudes and available combinations to produce said defibrillation sequence.

3. An apparatus as claimed in claim 2, further comprising electrode switching means for selectively connecting one of said plurality of defibrillation electrodes as a return electrode for said stimulation pulses.

4. An apparatus as claimed in claim 3 further comprising an apparatus case electrically connected to said output means adapted for implantation in a patient, and wherein said electrode switching means comprises means for selecting one of said plurality of said defibrillation electrodes or said apparatus case as said return electrode.

5. An apparatus as claimed in claim 3 wherein said memory means comprises means for storing a selection of said defibrillation electrodes for connection as said return electrode, and wherein said microprocessor means comprises means for controlling said electrode switching means dependent on the stored data for connecting one of said defibrillation electrodes as said return electrode.

6. An apparatus as claimed in claim 5, wherein said microprocessor means comprises means for controlling said electrode switching means for connecting a different one of said defibrillation electrodes as said return electrode between each stimulation pulse in said defibrillation sequence.

7. An apparatus as claimed in claim 5, wherein said microprocessor means comprises means for controlling said electrode switching means for connecting a different one of said defibrillation electrodes as said return electrode between groups of stimulation pulses in said defibrillation sequence.

8. An apparatus as claimed in claim 1, wherein said means for delivering defibrillation shocks includes pulse generating circuitry having energy-storing capacitors, and wherein said output means comprises pulse generating circuitry identical to said pulse generator circuitry in said means for delivering defibrillation shocks but with energy-storing capacitors having a capacitance less than the energy-storing capacitors in said means for delivering defibrillation shocks.

9. An apparatus as claimed in claim 1, wherein said control means comprises means for controlling delivery of said stimulation pulses at an interval having a duration which is a fraction of the refractory period of a heart cell.

10. An apparatus as claimed in claim 1, wherein said control means comprises means for controlling delivery of said stimulation pulses and said defibrillation shocks for producing a series of said stimulation pulses before each defibrillation shock.

11. An apparatus as claimed in claim 1, wherein said pacing electrode comprises an endocardiac electrode.

12. An apparatus as claimed in claim 1, wherein said pacing electrode comprises an epicardiac electrode.

13. An apparatus as claimed in claim 1, wherein said defibrillation electrodes respectively comprise patch electrodes.

14. An apparatus as claimed in claim 1, wherein said defibrillation electrodes comprise a combination of patch electrodes and intracardiac electrodes.

15. An apparatus as claimed in claim 1, wherein said output means comprises means for generating stimulation pulses having an energy content of approximately 1 millijoule.

16. An apparatus as claimed in claim 1 further comprising electrode switching means for selectively connecting one of said plurality of defibrillation electrodes as a return electrode for said stimulation pulses.

17. An apparatus as claimed in claim 16 further comprising an apparatus case electrically connected to said output means and adapted for implantation in a patient, and wherein said electrode switching means comprises means for selecting one of said plurality of defibrillation electrodes or said apparatus case as said return electrode.

18. An apparatus as claimed in claim 4 wherein said memory means comprises means for storing a selection of said defibrillation electrodes or said apparatus case for connection as said return electrode, and wherein said microprocessor means comprises means for controlling said electrode switching means dependent on the stored data for connecting one of said defibrillation electrodes or said apparatus case as said return electrode.

19. An apparatus as claimed in claim 18 wherein said microprocessor means comprises means for controlling said electrode switching means for connecting a different one of said defibrillation electrodes or said apparatus case as said return electrode between each stimulation pulse in said defibrillation sequence.

20. An apparatus as claimed in claim 18 wherein said microprocessor means comprises means for controlling said electrode switching means for connecting a different one of said defibrillation electrodes or said apparatus case as said return electrode between groups of stimulation pulses in said defibrillation sequence.

* * * * *